(12) United States Patent
Thompson

(10) Patent No.: US 11,530,423 B1
(45) Date of Patent: Dec. 20, 2022

(54) COMPOSITION FOR REGULATING PRODUCTION OF RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 17/727,405

(22) Filed: Apr. 22, 2022

(51) Int. Cl.
*C12N 15/86* (2006.01)
*A01N 63/00* (2020.01)
*C12N 7/00* (2006.01)
*A61K 39/00* (2006.01)
*A61K 48/00* (2006.01)

(52) U.S. Cl.
CPC .... *C12N 15/86* (2013.01); *C12N 2750/14143* (2013.01)

(58) Field of Classification Search
CPC .............. A61K 2300/00; A61K 38/177; A61K 38/178; A61K 38/191; A61K 38/193
See application file for complete search history.

*Primary Examiner* — Barry A Chestnut
(74) *Attorney, Agent, or Firm* — Gowling WLG (Canada) LLP

(57) ABSTRACT

The present disclosure relates to one or more compositions for increasing production of micro-RNA associated with decreasing production of a target biomolecule.

16 Claims, 12 Drawing Sheets

Specification includes a Sequence Listing.

SEQUENCE LISTING

<160> NUMBER OF SEQ ID NOS: 11

<210> SEQ ID NO 1
<211> LENGTH: 6237
<212> TYPE: DNA
<213> ORGANISM: Artificial Sequence
<220> FEATURE:
<223> OTHER INFORMATION: Synthetic Sequence

<400> SEQUENCE: 1

```
cagcagctgc gcgctcgctc gctcactgag gccgcccggg caaagcccgg gcgtcgggcg      60
acctttggtc gcccggcctc agtgagcgag cgagcgcgca gagagggagt ggccaactcc     120
atcactaggg gttccttgta gttaatgatt aacccgccat gctacttatc tacgtagcca     180
tgctctagga cattgattat tgactagtgg agttccgcgt tacataactt acggtaaatg     240
gcccgcctgg ctgaccgccc aacgacccc gcccattgac gtcaataatg acgtatgttc      300
ccatagtaac gccaataggg actttccatt gacgtcaatg ggtggagtat ttacggtaaa     360
ctgcccactt ggcagtacat caagtgtatc atatgccaag tacgccccct attgacgtca     420
atgacggtaa atggcccgcc tggcattatg cccagtacat gaccttatgg gactttccta     480
cttggcagta catctacgta ttagtcatcg ctattaccat ggtcgaggtg agccccacgt     540
tctgcttcac tctccccatc tccccccct ccccaccccc aattttgtat ttatttattt     600
tttaattatt ttgtgcagcg atgggggcgg ggggggggg gggcgcgcgc caggcggggc     660
ggggcggggc gaggggcggg gcggggcgag gcggagaggt gcggcggcag ccaatcagag     720
cggcgcgctc cgaaagtttc cttttatggc gaggcggcgg cggcggcggc cctataaaaa     780
gcgaagcgcg cggcgggcgg gagtcgctgc gcgctgcctt cgccccgtgc cccgctccgc     840
cgccgcctcg cgccgcccgc cccggctctg actgaccgcg ttactaaaac aggtaagtcc     900
ggcctccgcg ccgggttttg gcgcctcccg cgggcgcccc cctcctcacg gcgagcgctg     960
ccacgtcaga cgaagggcgc agcgagcgtc ctgatccttc cgcccggacg ctcaggacag    1020
cggcccgctg ctcataagac tcggccttag aaccccagta tcagcagaag gacattttag    1080
gacgggactt gggtgactct agggcactgg ttttctttcc agagagcgga acaggcgagg    1140
aaaagtagtc ccttctcggc gattctgcgg agggatctcc gtgggcggt gaacgccgat    1200 gatgcctcta ctaaccatgt tcatgttttc tttttttttc tacaggtcct gggtgacgaa    1260
caggcctagc atcgataccg tcgtatgtgc tggaggcttc tgaaggctg tatgctggct    1320 cctccacttg gtggtttggt tttggcctct gactgaccaa accacagtgg aggagccagg    1380
acacaaggcc tgttactagc actcacatgg aacaaatggc ctctagcctg gaggcttgct    1440
gaaggctgta tgctgttttct cctggtatga gatagcgttt tggcctctga ctgacgctat    1500
ctcaccagga gaaacaggac acaaggcctg ttactagcac tcacatggaa caaatggcct    1560
```

```
ctagcctgga ggcttgctga aggctgtatg ctgccgcaaa gtctaagtac ttgggttttg    1620
gcctctgact gacccaagta cagactttgc ggcaggacac aaggcctgtt actagcactc    1680
acatggaaca aatggcctct ctagaataat caacctctgg attacaaaat ttgtgaaaga    1740
ttgactggta ttcttaacta tgttgctcct tttacgctat gtggatacgc tgctttaatg    1800
cctttgtatc atgctattgc ttcccgtatg gctttcattt tctcctcctt gtataaatcc    1860
tggttgctgt ctctttatga ggagttgtgg cccgttgtca ggcaacgtgg cgtggtgtgc    1920
actgtgtttg ctgacgcaac ccccactggt tggggcattg ccaccacctg tcagctcctt    1980
tccgggactt tcgctttccc cctccctatt gccacggcgg aactcatcgc cgcctgcctt    2040
gcccgctgct ggacaggggc tcggctgttg ggcactgaca attccgtggt gttgtcgggg    2100
aaatcatcgt cctttccttg gctgctcgcc tgtgttgcca cctggattct gcgcgggacg    2160
tccttctgct acgtcccttc ggccctcaat ccagcggacc ttccttcccg cggcctgctg    2220
ccggctctgc ggcctcttcc gcgtcttcgc cttcgccctc agacgagtcg gatctccctt    2280
tgggccgcct ccccgcctaa gcttatcgat accgtcgaga tctaacttgt ttattgcagc    2340
ttataatggt tacaaataaa gcaatagcat cacaaatttc acaaataaag cattttttc    2400 actgcattct agttgtggtt tgtccaaact catcaatgta tcttatcatg tctggatctc    2460
gacctcgact agagcatggc tacgtagata agtagcatgg cgggttaatc attaactaca    2520
aggaacccct agtgatggag ttggccactc cctctctgcg cgctcgctcg ctcactgagg    2580
ccgggcgacc aaaggtcgcc cgacgcccgg gctttgcccg gcggcctcca gtgagcgagc    2640
gagcgcgcag ctggcgtaat agcgaagagg cccgcaccga tcgcccttcc caacagttgc    2700
gcagcctgaa tggcgaatgg cgattccgtt gcaatggctg gcggtaatat tgttctggat    2760
attaccagca aggccgatag tttgagttct tctactcagg caagtgatgt tattactaat    2820
caaagaagta ttgcgacaac ggttaatttg cgtgatggac agactctttt actcggtggc    2880
ctcactgatt ataaaaacac ttctcaggat tctggcgtac cgttcctgtc taaaatccct    2940
ttaatcggcc tcctgtttag ctcccgctct gattctaacg aggaaagcac gttatacgtg    3000
ctcgtcaaag caaccatagt acgcgccctg tagcggcgca ttaagcgcgg cgggtgtggt    3060
ggttacgcgc agcgtgaccg ctacacttgc cagcgcccta gcgcccgctc ctttcgcttt    3120
cttcccttcc tttctcgcca cgttcgccgg ctttccccgt caagctctaa atcgggggct    3180
ccctttaggg ttccgattta gtgctttacg gcacctcgac cccaaaaaac ttgattaggg    3240
tgatggttca cgtagtgggc catcgccctg atagacggtt tttcgccctt tgacgttgga    3300
gtccacgttc tttaatagtg gactcttgtt ccaaactgga acaacactca accctatctc    3360
ggtctattct tttgatttat aagggatttt gccgatttcg gcctattggt taaaaaatga    3420
gctgatttaa caaaaattta acgcgaattt taacaaaata ttaacgttta catttaaat    3480 atttgcttat acaatcttcc tgttttgggg cttttctga ttatcaaccg ggtacatat    3540 gattgacatg ctagttttac gattaccgtt catcgattct cttgtttgct ccagactctc    3600
aggcaatgac ctgatagcct ttgtagagac ctctcaaaaa tagctaccct ctccggcatg    3660
aatttatcag ctagaacggt tgaatatcat attgatggtg atttgactgt ctccggcctt    3720
tctcacccgt ttgaatcttt acctacacat tactcaggca ttgcatttaa aatatatgag    3780
ggttctaaaa atttttatcc ttgcgttgaa ataaaggctt ctcccgcaaa agtattacag    3840
ggtcataatg ttttttggtac aaccgattta gctttatgct ctgaggcttt attgcttaat    3900
```

```
tttgctaatt ctttgccttg cctgtatgat ttattggatg ttggaattcc tgatgcggta      3960
ttttctcctt acgcatctgt gcggtatttc acaccgcata tggtgcactc tcagtacaat      4020
ctgctctgat gccgcatagt taagccagcc ccgacacccg ccaacacccg ctgacgcgcc      4080
ctgacgggct tgtctgctcc cggcatccgc ttacagacaa gctgtgaccg tctccgggag      4140
ctgcatgtgt cagaggtttt caccgtcatc accgaaacgc gcgagacgaa agggcctcgt      4200
gatacgccta tttttatagg ttaatgtcat gataataatg gtttcttaga cgtcaggtgg      4260
cacttttcgg ggaaatgtgc gcggaacccc tatttgttta ttttttctaaa tacattcaaa      4320 tatgtatccg ctcatgagac aataaccctg ataaatgctt caataatatt gaaaaaggaa      4380
gagtatgagt attcaacatt tccgtgtcgc ccttattccc ttttttgcgg cattttgcct      4440
tcctgttttt gctcacccag aaacgctggt gaaagtaaaa gatgctgaag atcagttggg      4500
tgcacgagtg ggttacatcg aactggatct caacagcggt aagatccttg agagttttcg      4560
ccccgaagaa cgttttccaa tgatgagcac ttttaaagtt ctgctatgtg gcgcggtatt      4620
atcccgtatt gacgccgggc aagagcaact cggtcgccgc atacactatt ctcagaatga      4680
cttggttgag tactcaccag tcacagaaaa gcatcttacg gatggcatga cagtaagaga      4740
attatgcagt gctgccataa ccatgagtga taacactgcg gccaacttac ttctgacaac      4800
gatcggagga ccgaaggagc taaccgcttt tttgcacaac atgggggatc atgtaactcg      4860
ccttgatcgt tgggaaccgg agctgaatga agccatacca aacgacgagc gtgacaccac      4920
gatgcctgta gcaatggcaa caacgttgcg caaactatta actggcgaac tacttactct      4980
agcttcccgg caacaattaa tagactggat ggaggcggat aaagttgcag gaccacttct      5040
gcgctcggcc cttccggctg gctggtttat tgctgataaa tctggagccg gtgagcgtgg      5100
gtctcgcggt atcattgcag cactggggcc agatggtaag ccctcccgta tcgtagttat      5160
ctacacgacg gggagtcagg caactatgga tgaacgaaat agacagatcg ctgagatagg      5220
tgcctcactg attaagcatt ggtaactgtc agaccaagtt tactcatata ctttagat       5280 tgatttaaaa cttcattttt aatttaaaag gatctaggtg aagatccttt tgataatct       5340 catgaccaaa atcccttaac gtgagttttc gttccactga gcgtcagacc ccgtagaaaa      5400
gatcaaagga tcttcttgag atcctttttt tctgcgcgta atctgctgct tgcaaacaaa      5460
aaaaccaccg ctaccagcgg tggtttgttt gccggatcaa gagctaccaa ctctttttcc      5520
gaaggtaact ggcttcagca gagcgcagat accaaatact gtccttctag tgtagccgta      5580
gttaggccac cacttcaaga actctgtagc accgcctaca tacctcgctc tgctaatcct      5640
gttaccagtg gctgctgcca gtggcgataa gtcgtgtctt accgggttgg actcaagacg      5700
atagttaccg gataaggcgc agcggtcggg ctgaacgggg ggttcgtgca cacagcccag      5760
cttggagcga acgacctaca ccgaactgag atacctacag cgtgagctat gagaaagcgc      5820
cacgcttccc gaagggagaa aggcggacag gtatccggta agcggcaggg tcggaacagg      5880
agagcgcacg agggagcttc caggggggaaa cgcctggtat ctttatagtc ctgtcgggtt      5940
tcgccacctc tgacttgagc gtcgattttt gtgatgctcg tcaggggggc ggagcctatg      6000
gaaaaacgcc agcaacgcgg ccttttttacg gttcctggcc ttttgctggc cttttgctca      6060
catgttcttt cctgcgttat cccctgattc tgtggataac cgtattaccg cctttgagtg      6120
agctgatacc gctcgccgca gccgaacgac cgagcgcagc gagtcagtga gcgaggaagc      6180
ggaagagcgc ccaatacgca aaccgcctct ccccgcgcgt tggccgattc attaatg        6237
```

```
<210> SEQ ID NO 2
<211> LENGTH: 417
<212> TYPE: DNA
<213> ORGANISM: Artificial Sequence
<220> FEATURE:
<223> OTHER INFORMATION: Synthetic Sequence

<400> SEQUENCE: 2
ctggaggctt gctgaaggct gtatgctggc tcctccactt ggtggtttgg ttttggcctc      60
tgactgacca aaccacagtg gaggagccag gacacaaggc ctgttactag cactcacatg     120
gaacaaatgg cctctagcct ggaggcttgc tgaaggctgt atgctgtttc tcctggtatg     180
agatagcgtt ttggcctctg actgacgcta tctcaccagg agaaacagga cacaaggcct     240
gttactagca ctcacatgga acaaatggcc tctagcctgg aggcttgctg aaggctgtat     300
gctgccgcaa agtctaagta cttgggtttt ggcctctgac tgacccaagt acagactttg     360
cggcaggaca caaggcctgt tactagcact cacatggaac aaatggcctc tctagaa        417

<210> SEQ ID NO 3
<211> LENGTH: 139
<212> TYPE: DNA
<213> ORGANISM: Artificial Sequence
<220> FEATURE:
<223> OTHER INFORMATION: Synthetic Sequence

<400> SEQUENCE: 3
ctggaggctt gctgaaggct gtatgctggc tcctccactt ggtggtttgg ttttggcctc      60
tgactgacca aaccacagtg gaggagccag gacacaaggc ctgttactag cactcacatg     120
gaacaaatgg cctctagcc                                                  139

<210> SEQ ID NO 4
<211> LENGTH: 137
<212> TYPE: DNA
<213> ORGANISM: Artificial Sequence
<220> FEATURE:
<223> OTHER INFORMATION: Synthetic Sequence

<400> SEQUENCE: 4
tggaggcttg ctgaaggctg tatgctgttt ctcctggtat gagatagcgt tttggcctct      60
gactgacgct atctcaccag gagaaacagg acacaaggcc tgttactagc actcacatgg     120
aacaaatggc ctctagc                                                    137

<210> SEQ ID NO 5
<211> LENGTH: 141
<212> TYPE: DNA
<213> ORGANISM: Artificial Sequence
<220> FEATURE:
<223> OTHER INFORMATION: Synthetic Sequence

<400> SEQUENCE: 5
ctggaggctt gctgaaggct gtatgctgcc gcaaagtcta agtacttggg ttttggcctc      60
tgactgaccc aagtacagac tttgcggcag gacacaaggc ctgttactag cactcacatg     120
gaacaaatgg cctctctaga a                                               141

<210> SEQ ID NO 6
<211> LENGTH: 21
<212> TYPE: DNA
<213> ORGANISM: Artificial Sequence
<220> FEATURE:
<223> OTHER INFORMATION: Synthetic Sequence
```

```
<400> SEQUENCE: 6
gctcctccac ttggtggttt g                                              21

<210> SEQ ID NO 7
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 7
caaaccacag tggaggagc                                                 19

<210> SEQ ID NO 8
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 8
tttctcctgg tatgagatag c                                              21

<210> SEQ ID NO 9
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 9
gctatctcac caggagaaa                                                 19

<210> SEQ ID NO 10
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 10
ccgcaaagtc taagtacttg g                                              21

<210> SEQ ID NO 11
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 11
ccaagtacag actttgcgg                                                 19
```

COMPOSITION FOR REGULATING PRODUCTION OF RIBONUCLEIC ACID

TECHNICAL FIELD

The present disclosure generally relates to compositions for regulating production of ribonucleic acid (RNA). In particular, the present disclosure relates to compositions and methods for regulating gene expression and, therefore, production of micro-RNA.

BACKGROUND

Bioactive molecules, including enzymes, receptors, receptor agonists and antagonists, are necessary for the homeostatic control of biological systems.

When bioactive molecules are over-expressed, under-expressed or mis-expressed, homeostasis is lost, and disease is often the result.

Known approaches to the treatment of conditions whereby bioactive molecules are over or mis-expressed are the commercially available pharmaceutical products that bind to and block the production or effectiveness of one or more bioactive molecules.

SUMMARY

Some embodiments of the present disclosure relate to one or more compositions that upregulate the production of one or more sequences of micro-ribonucleic acid (miRNA). The sequences of miRNA may be complimentary to a sequence of target messenger RNA (mRNA) that encodes for translation of a target biomolecule and the miRNA can cause the target mRNA to be degraded or inactivated, thereby causing a decrease in production of the target biomolecule by a subject that is administered the one or more compositions. In some embodiments of the present disclosure, the target biomolecule is a cytokine. In some embodiments of the present disclosure, the target biomolecule is a pro-inflammatory cytokine, such as tumor necrosis factor alpha (TNF-alpha).

In some embodiments of the present disclosure the compositions comprise vector DNA that includes one or more an insert sequences of nucleic acids that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation of the target biomolecule by one or more of the subject's cells.

Some embodiments of the present disclosure relate to compositions that upregulate the production of miRNA that degrades, or causes degradation of, or inactivates or causes the inactivation of the target mRNA of the target biomolecule.

Some embodiments of the present disclosure relate to compositions that can be used as a therapy or a treatment for a subject that has a condition whereby the target biomolecule is over or mis-expressed.

Some embodiments of the present disclosure relate to a recombinant plasmid (RP). In some embodiments of the present disclosure, the RP comprises a nucleotide sequence of SEQ ID No. 1. The RP comprises a nucleotide sequence encoding one or more nucleotide sequences encoding a miRNA sequence that targets mRNA of tumor necrosis alpha TNF-alpha; and an inverted terminal repeat.

Some embodiments of the present disclosure relate to a cassette, which may also be referred to as an insert, for use with an RP, wherein the cassette comprises a nucleotide sequence of SEQ ID No. 2. When the cassette with SEQ ID No. 2 is included in the RP and the RP is administered to a subject, one or more of the subject's cells will upregulate production of miRNA that degrades, or causes degradation of, or inactivates or causes the inactivation of the target mRNA of the target biomolecule. For example, the target biomolecule may be TNF-alpha.

Some embodiments of the present disclosure relate to a cassette for use with an RP, wherein the cassette comprises a nucleotide sequence of SEQ ID No. 3. When the cassette with SEQ ID No. 3 is included in the RP and the RP is administered to a subject, one or more of the subject's cells will upregulate production of at least a portion of a miRNA sequence that degrades, or causes degradation of, or inactivates or causes the inactivation of the target mRNA of the target biomolecule. For example the target biomolecule may be TNF-alpha.

Some embodiments of the present disclosure relate to a cassette for use with an RP, wherein the cassette comprises a nucleotide sequence of SEQ ID No. 4. When the cassette with SEQ ID No. 4 is included in the RP and the RP is administered to a subject, one or more of the subject's cells will upregulate production of at least a portion of a miRNA sequence that degrades, or causes degradation of, or inactivates or causes the inactivation of the target mRNA of the target biomolecule. For example, the target biomolecule may be TNF-alpha.

Some embodiments of the present disclosure relate to a cassette for use with an RP, wherein the cassette comprises a nucleotide sequence of SEQ ID No. 5. When the cassette with SEQ ID No. 5 is included in the RP and the RP is administered to a subject, one or more of the subject's cells will upregulate production of at least a portion of a miRNA sequence that degrades, or causes degradation of, or inactivates or causes the inactivation of the target mRNA of the target biomolecule. For example, the target biomolecule may be TNF-alpha.

Some embodiments of the present disclosure relate to a method of making an composition/target cell complex. The method comprising a step of administering a RP comprising SEQ ID No. 1 to a target cell for forming the composition/target cell complex, wherein the composition/target cell complex causes the target cell to increase production of a one or more sequences of micro ribonucleic acid (miRNA) that decreases production of a target biomolecule.

Embodiments of the present disclosure relate to at least one approach for inducing endogenous production of one or more sequences of miRNA that target and silence mRNA of a target biomolecule, for example the TNF-alpha protein. A first approach utilizes gene vectors containing nucleotide sequences for increasing the endogenous production one or more sequences of miRNA, complete or partial sequences, that target and silence the mRNA of TNF-alpha, which can be administered to a subject to increase the subject's production of one or more sequences of the miRNA.

BRIEF DESCRIPTION OF THE DRAWINGS

These and other features of the present disclosure will become more apparent in the following detailed description in which reference is made to the appended drawings.

Figure 1:
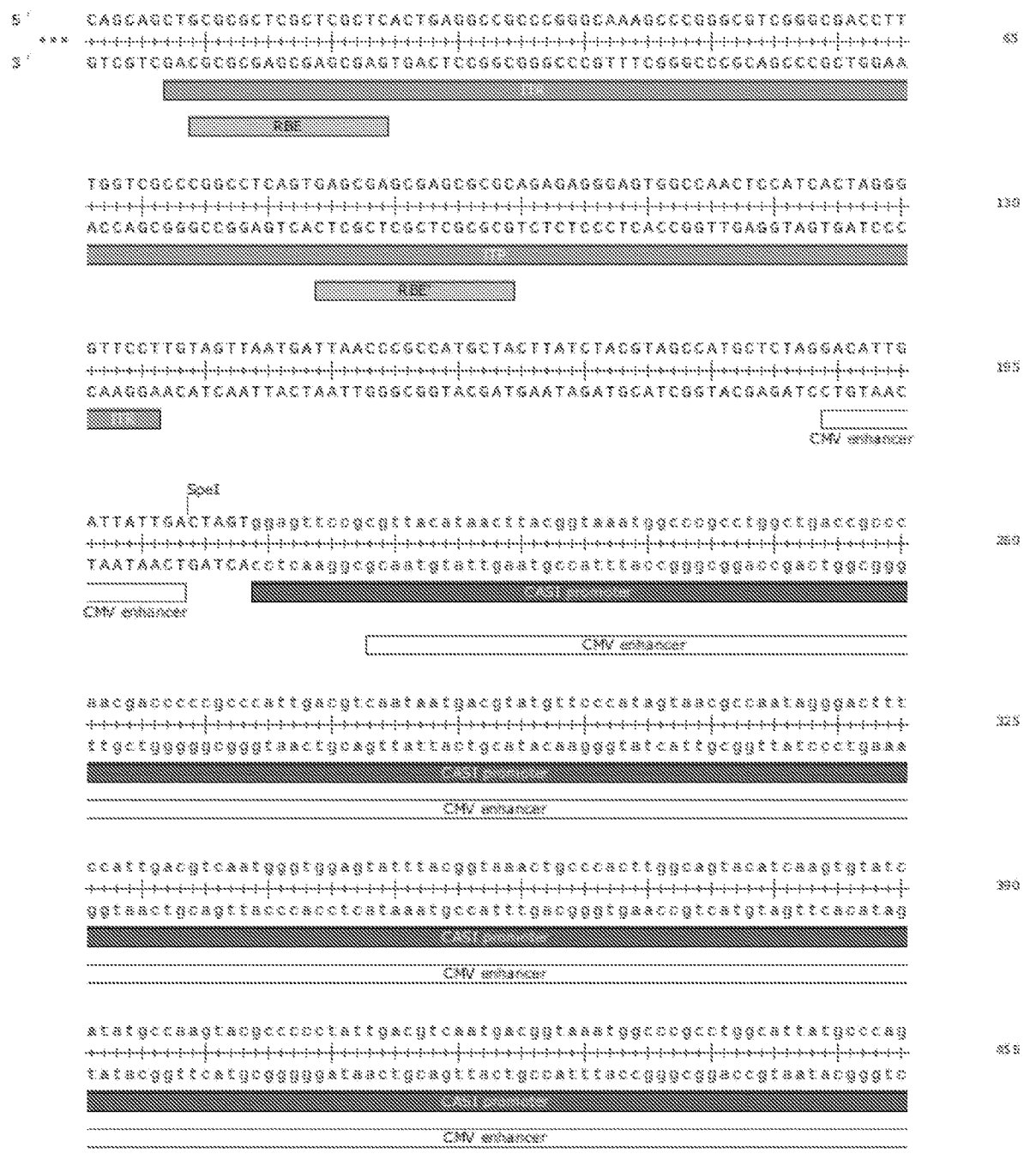

FIG. 1 is a schematic that represents a first portion of a recombinant plasmid (RP), according to embodiments of the present disclosure.

Figure 2:
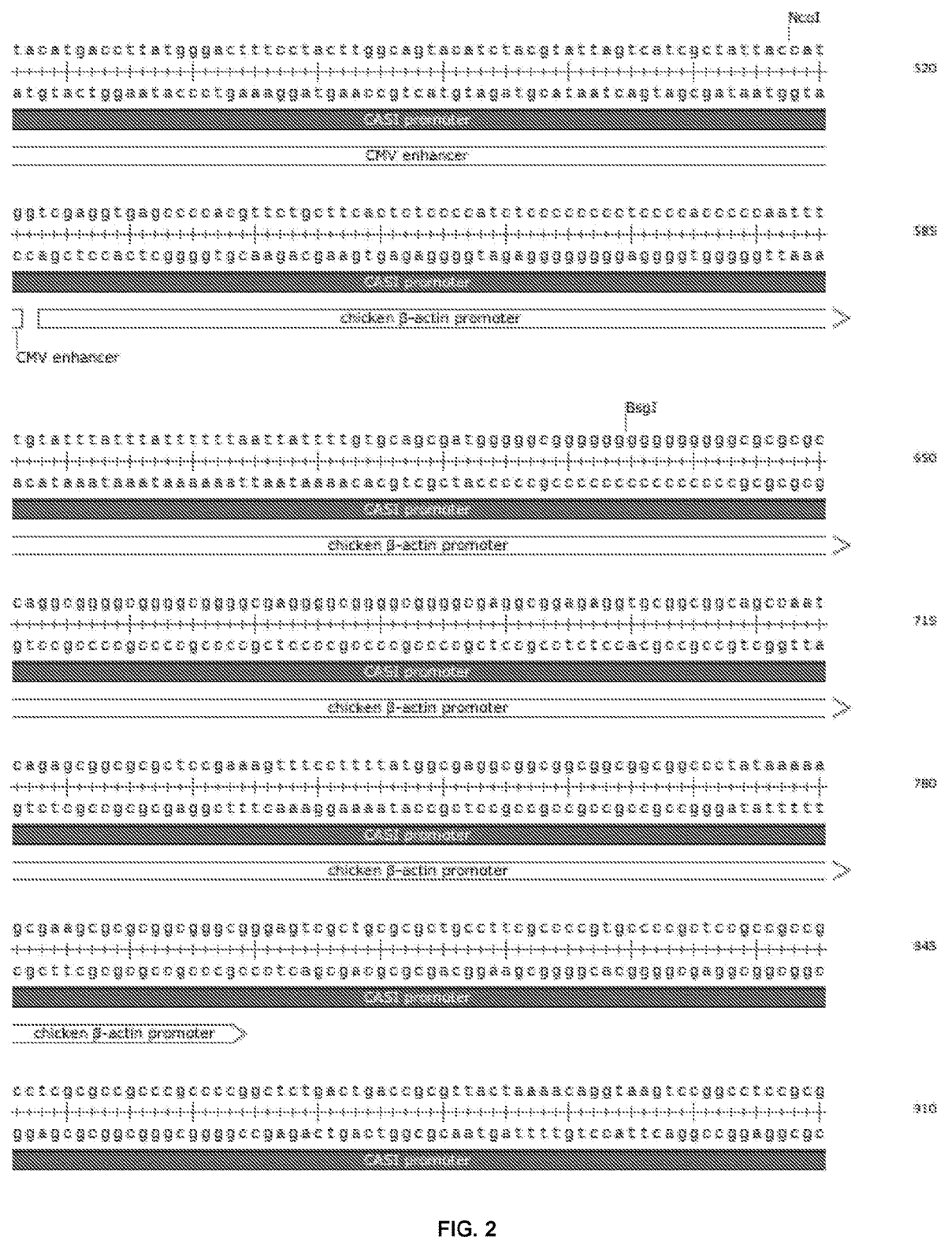

FIG. 2 is a schematic that represents a second portion of an RP, according to embodiments of the present disclosure, which is contiguous with the first portion of FIG. 1.

Figure 3:
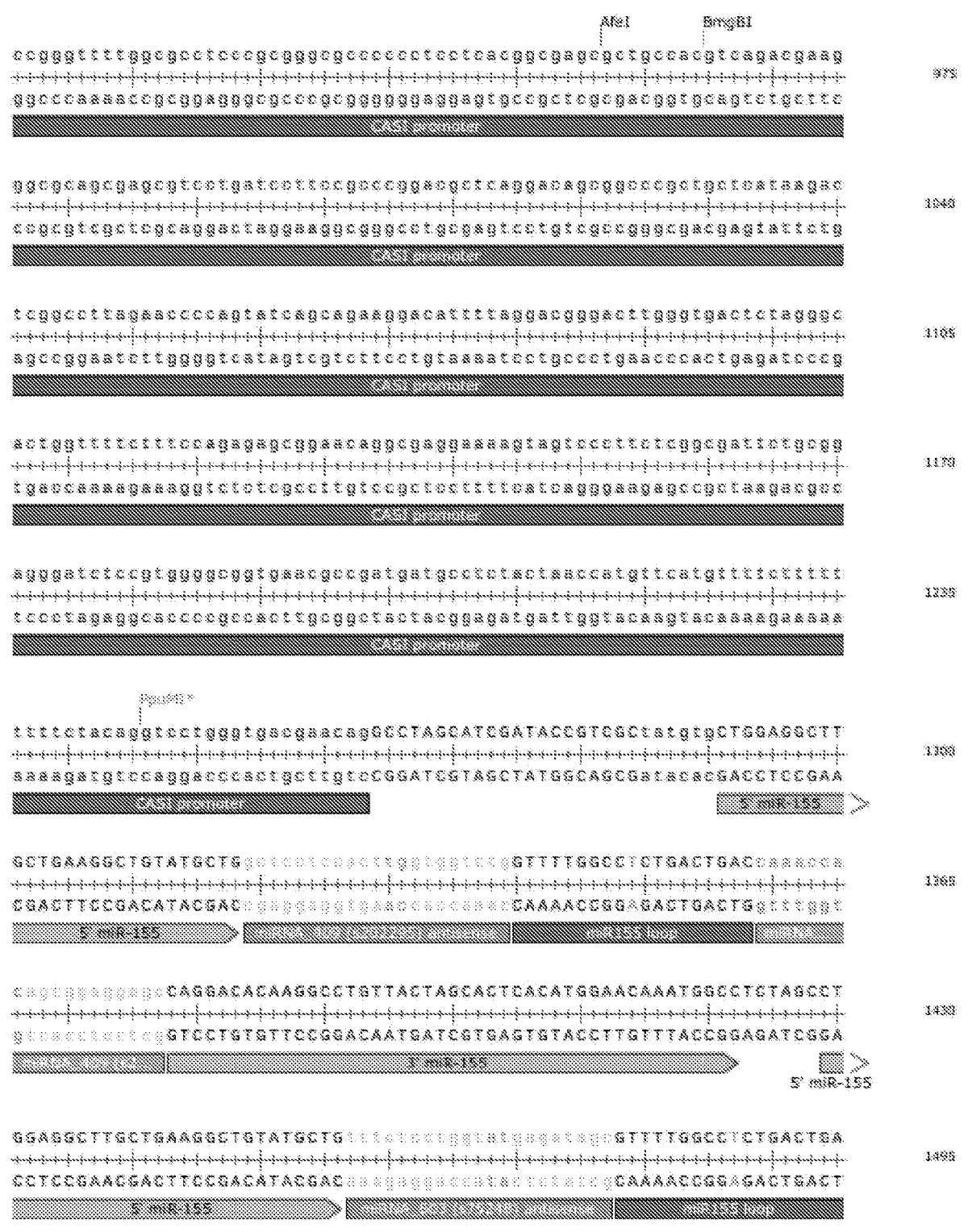

FIG. 3 is a schematic that represents a third portion of an RP, according to embodiments of the present disclosure, which is contiguous with the second portion of FIG. 2.

Figure 4:
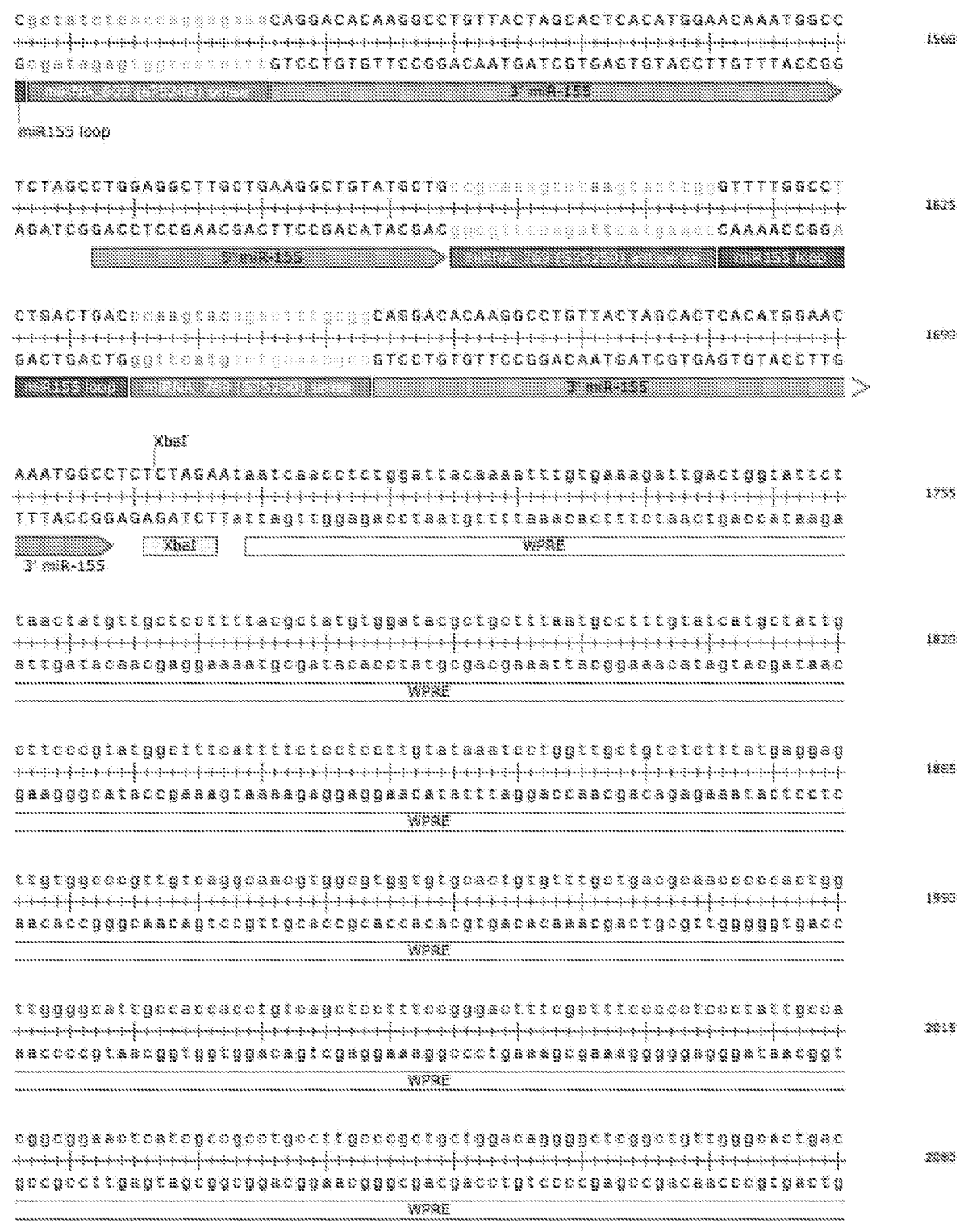

FIG. 4 is a schematic that represents a fourth portion of an RP, according to embodiments of the present disclosure, which is contiguous with the third portion of FIG. 3.

Figure 5:
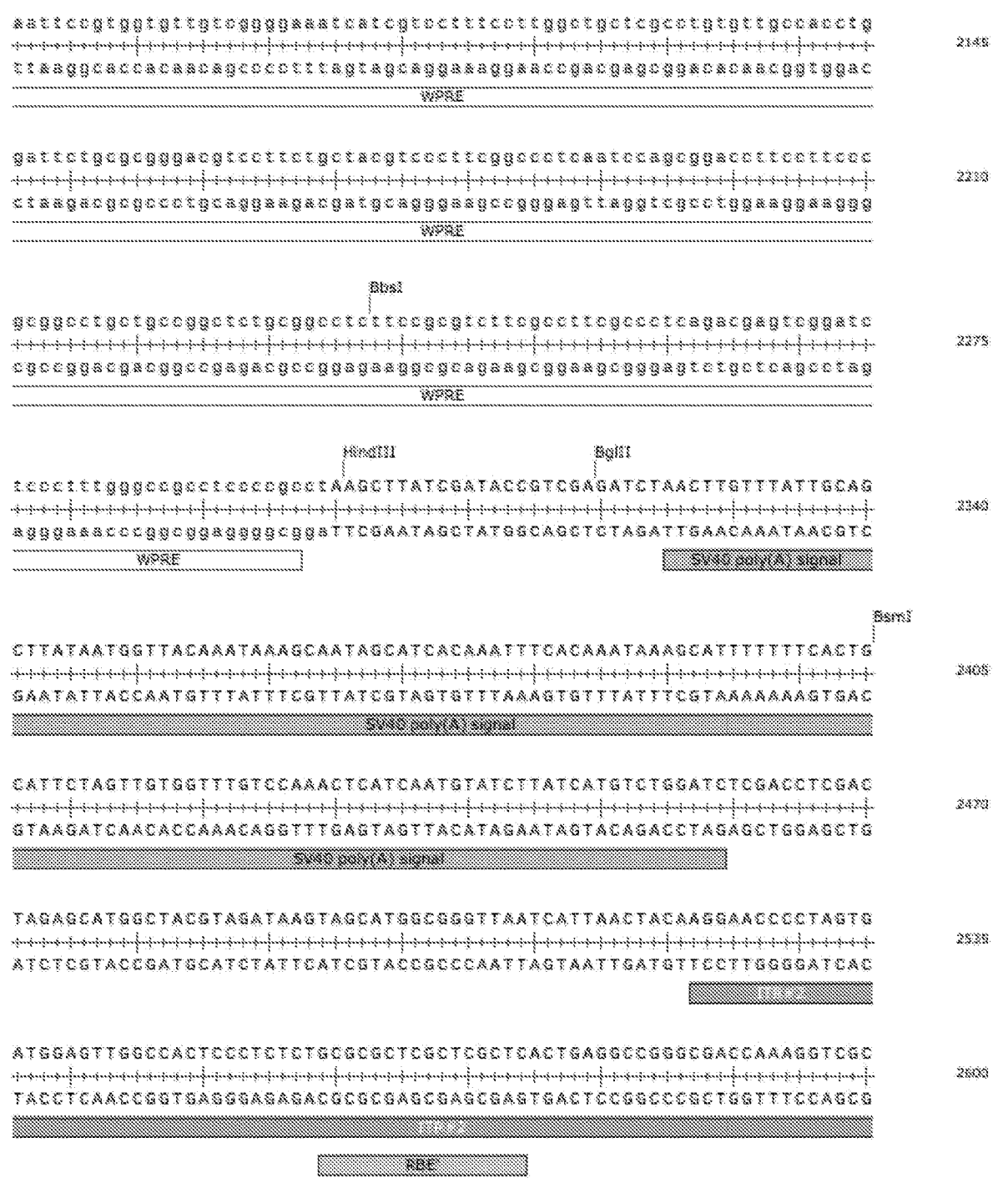

FIG. 5 is a schematic that represents a fifth portion of an RP, according to embodiments of the present disclosure, which is contiguous with the fourth portion of FIG. 4.

Figure 7:
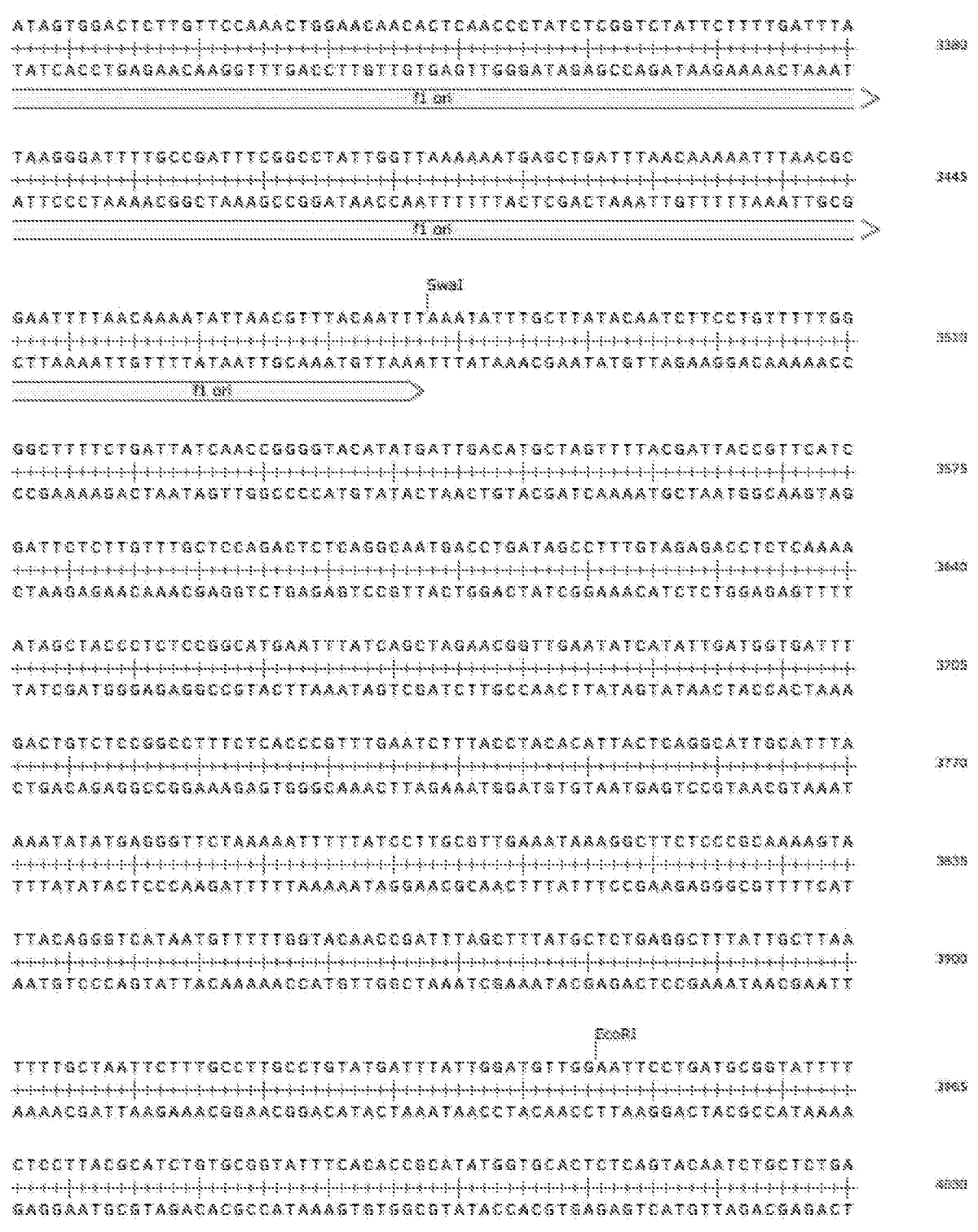

FIG. 7 is a schematic that represents a seventh portion of an RP, according to embodiments of the present disclosure, which is contiguous with the sixth portion of FIG. 6.

Figure 8:
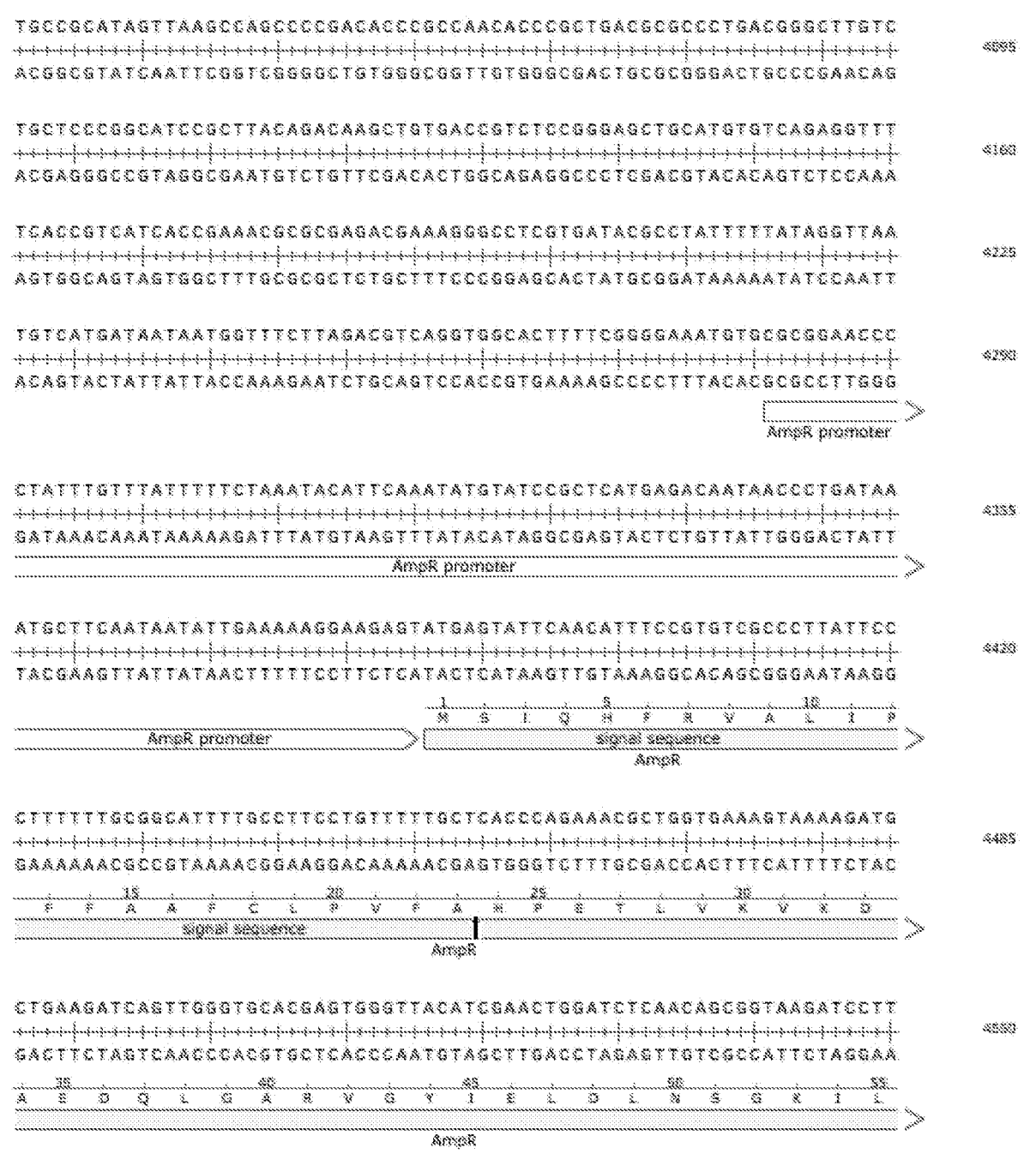

FIG. 8 is a schematic that represents an eighth portion of an RP, according to embodiments of the present disclosure, which is contiguous with the seventh portion of FIG. 7.

Figure 10:
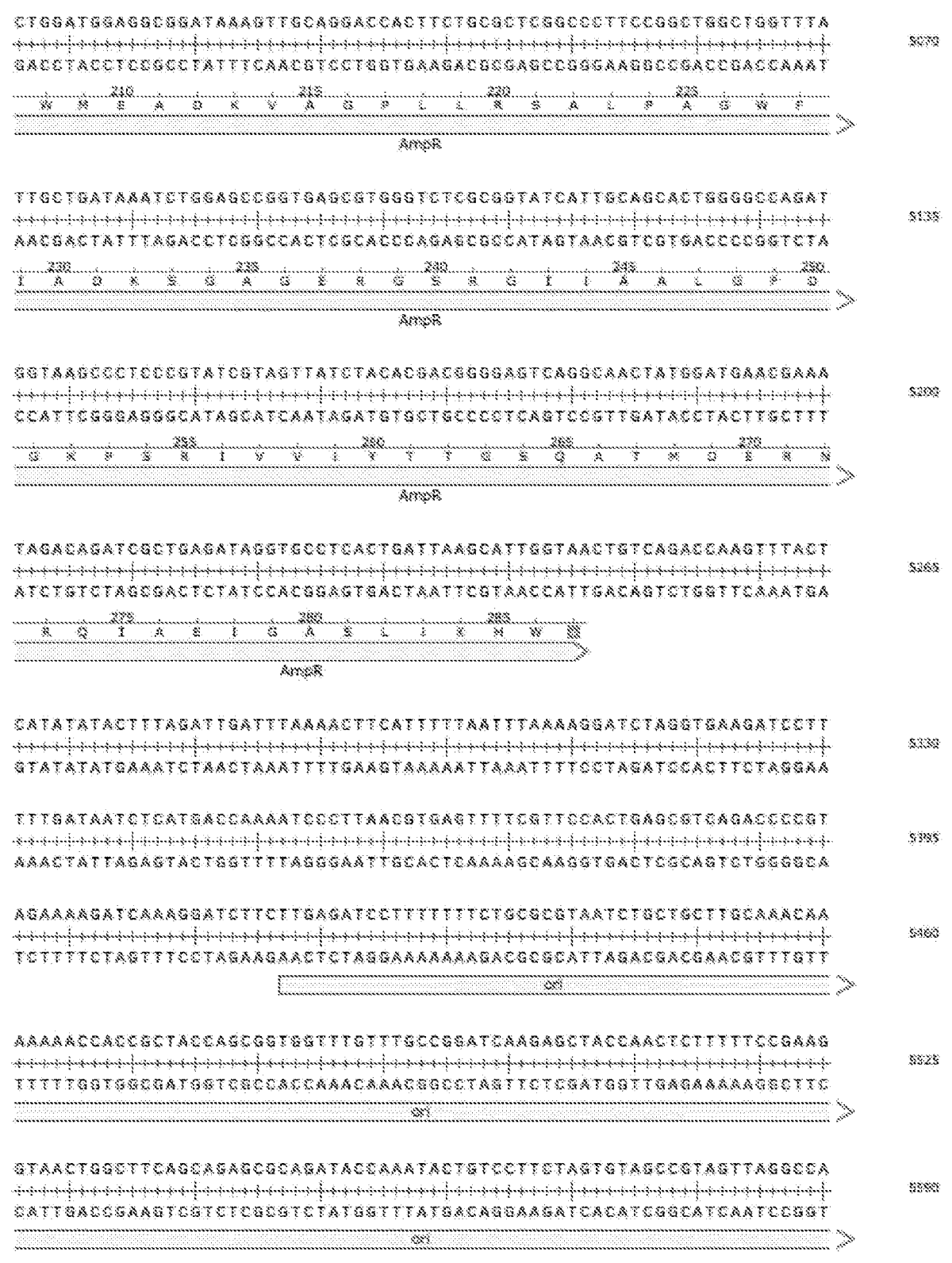

FIG. 10 is a schematic that represents a tenth portion of an RP, according to embodiments of the present disclosure, which is contiguous with the ninth portion of FIG. 9.

Figure 11:
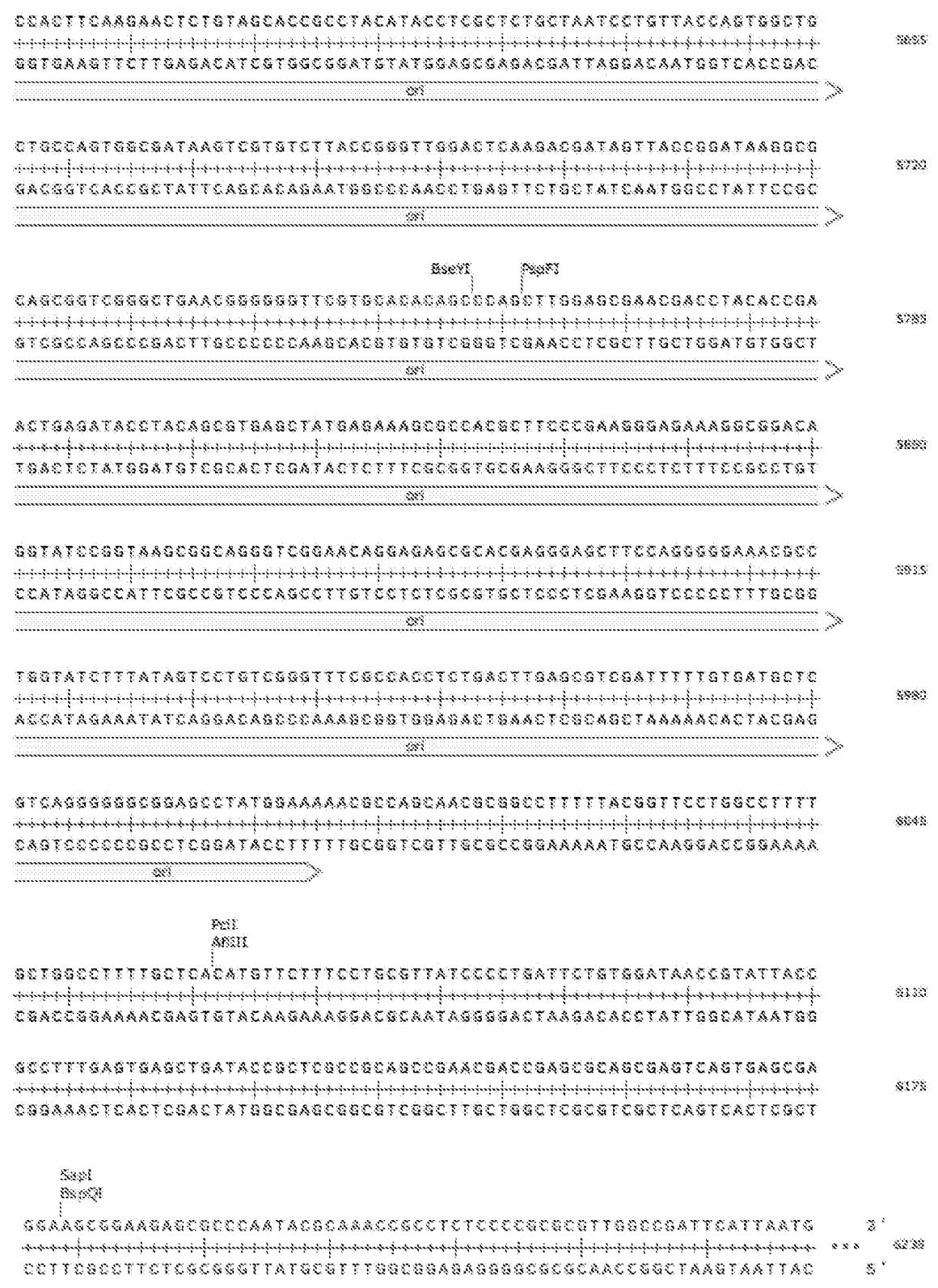

FIG. 11 is a schematic that represents an eleventh portion of an RP, according to embodiments of the present disclosure, which is contiguous with the tenth portion of FIG. 10.

FIG. 12 is a schematic that represents a twelfth portion of an RP, according to embodiments of the present disclosure, which is contiguous with the eleventh portion of FIG. 11.

DETAILED DESCRIPTION

Figure 6:
FIG. 6 is a schematic that represents a sixth portion of an RP, according to embodiments of the present disclosure, which is contiguous with the fifth portion of FIG. 5.

Unless defined otherwise, all technical and scientific terms used herein have the meanings that would be commonly understood by one of skill in the art in the context of the present description. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

As used herein, the singular forms "a", "an", and "the" include plural references unless the context clearly dictates otherwise. For example, reference to "an composition" includes one or more compositions and reference to "a subject" or "the subject" includes one or more subjects.

As used herein, the terms "about" or "approximately" refer to within about 25%, preferably within about 20%, preferably within about 15%, preferably within about 10%, preferably within about 5% of a given value or range. It is understood that such a variation is always included in any given value provided herein, whether or not it is specifically referred to.

As used herein, the term "activity" is used interchangeably with the term "functionality" and both terms refer to the physiologic action of biomolecule.

As used herein, the term "composition" refers to a substance that, when administered to a subject, causes one or more chemical reactions and/or one or more physical reactions and/or or one or more physiological reactions and/or one or more immunological reactions in the subject. In some embodiments of the present disclosure, the composition is a plasmid vector.

As used herein, the term "ameliorate" refers to improve and/or to make better and/or to make more satisfactory.

As used herein, the term "biomolecule" refers to a carbohydrate, a protein, an amino acid sequence, a nucleic acid, a lipid, a primary metabolite, a secondary metabolite or another metabolite that is found within a subject. A biomolecule may be endogenous or exogenous to a subject.

As used herein, the term "cell" refers to a single cell as well as a plurality of cells or a population of the same cell type or different cell types. Administering an composition to a cell includes in vivo, in vitro and ex vivo administrations and/or combinations thereof.

As used herein, the term "complex" refers to an association, either direct or indirect, between one or more particles of an composition and one or more target cells. This association results in a change in the metabolism of the target cell. As used herein, the phrase "change in metabolism" refers to an increase or a decrease in the one or more target cells' production of deoxyribonucleic acid (DNA), ribonucleic acid (RNA), one or more proteins, and/or any post-translational modifications of one or more proteins.

As used herein, the term "endogenous" refers to the production and/or modification of a molecule that originates within a subject.

As used herein, the term "exogenous" refers to a molecule that is within a subject but that did not originate within the subject. As used herein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also be used herein to refer to the functionality of a regulatory molecule, unless the context reasonably indicates otherwise.

As used herein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue and/or biological fluids.

As used herein, the term "target cell" refers to one or more cells and/or cell types that are deleteriously affected, either directly or indirectly, by a dysregulated immune system and/or a disease process. The term "target cell" also refers to cells that are not deleteriously affected but that are the cells in which it is desired that the composition interacts.

As used herein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used herein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used herein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, an composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered by a viral vector. In some embodiments of the present disclosure, the vector is an adeno-associated virus vector.

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target-biomolecule protein is produced.

In some embodiments of the present disclosure, the target cytokine is a pro-inflammatory cytokine, meaning it has the physiologic effect of increasing inflammatory processes in the subject. In some embodiments of the present disclosure, the target cytokine is TNF-alpha. In some embodiments of the present disclosure, the target cytokine is an anti-inflammatory cytokine.

In some embodiments of the present disclosure, the insert comprises two or more nucleotide sequences that each encode one or more miRNA sequences that may be complimentary to and degrade, or cause degradation of, mRNA of the target biomolecule. In some embodiments of the present disclosure the insert comprises three nucleotide sequences that each encode a miRNA sequence that may be complimentary to and degrade, or causes degradation of, or inactivates or causes inactivation of mRNA of the target biomolecule.

In some embodiments of the present disclosure, the insert comprises one or more nucleotide sequences that each encode for a miRNA sequence that is complimentary to and degrades, or causes degradation of, or inactivates or causes inactivation of mRNA of the target biomolecule. In some embodiments of the present disclosure, the insert comprises two nucleotide sequences that each encode for miRNA that may be complimentary to and degrade, or causes degradation of, or inactivate, or causes inactivation of mRNA of the target biomolecule. In some embodiments of the present disclosure, the insert comprises three nucleotide sequences that each encode for miRNA that may be complimentary to and degrade, or causes degradation of, or inactivate, or causes inactivation of mRNA of the target biomolecule. In some embodiments of the present disclosure, the insert comprises more than three nucleotide sequences that each encode for miRNA that may be complimentary to and degrade, or causes degradation of, or inactivate, or causes inactivation of mRNA of the target biomolecule.

In some embodiments of the present disclosure, the composition can be administered to the subject by an intravenous route, an intramuscular route, an intraperitoneal route, an intrathecal route, an intravessical route, a topical route, an intranasal route, a transmucosal route, a pulmonary route, and combinations thereof.

In some embodiments of the present disclosure, the composition can be administered to the subject by pipetting a dose of the composition into an in vitro cell culture, perfusing or immersing an ex vivo cell or tissue preparation with a solution that comprises the composition, mixing a biological fluid sample with a solution or substrate that comprises the composition, or combinations thereof.

Some embodiments of the present disclosure relate to a composition that can be administered to a subject with a condition that results from, directly or indirectly, a dysregulated immune system. When a therapeutically effective amount of the composition is administered to the subject, the subject may change production and/or functionality of one or more immune system molecules. For example, the subject may decrease production and/or functionality of one or more immune system signaling molecules and/or one or more immune system effector molecules by changing the production of one or more sequences of DNA, one or more sequences of RNA and/or one or more proteins and/or one or more regulatory molecules that regulate the levels and/or functionality of the subject's immune system signaling molecules and/or immune system effector molecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two three, four, five, six, seven, eight, nine or ten miRNA sequences that each are complimentary to and degrade, or cause degradation of, one biomolecule, such as TNF-alpha. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that that cause increased production of one or more nucleotide sequences that cause an increased production of one or more miRNA sequences that that each are complimentary to and degrade, or cause degradation of, or inactivate, or cause inactivation of one biomolecule, such as TNF-alpha.

In some embodiments of the present disclosure, the delivery vehicle, also referred to as a vector, of the RP used for gene therapy is a virus that can be enveloped, or not (undeveloped), replication effective or not (replication ineffective), or combinations thereof. In some embodiments of the present disclosure, the vector is a virus that is not enveloped and not replication effective. In some embodiments of the present disclosure, the vector is a virus of the Paroviridae family. In some embodiments of the present disclosure, the vector is a virus of the genus Dependoparvaovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

The embodiments of the present disclosure also relate to administering a therapeutically effective amount of the composition. In some embodiments of the present disclosure, the therapeutically effective amount of the composition that is administered to a patient is between about 10 and about $1 \times 10^{16}$ TCID$_{50}$/kg (50% tissue culture infective dose per kilogram of the patient's body weight). In some embodiments of the present disclosure, the therapeutically effective amount of the composition that is administered to the patient is about $1 \times 10^{13}$ TCID$_{50}$/kg. In some embodiments of the present disclosure, the therapeutically effective amount of the composition that is administered to a patient is measured in TPC/kg (total particle count of the composition per kilogram of the patient's body weight). In some embodiments the therapeutically effective amount of the composition is between about 10 and about $1 \times 10^{16}$ TCP/kg.

Some embodiments of the present disclosure relate to an adenovirus associated virus (AAV) genome consisting of a RP that when operable inside a target cell will cause the target cell to produce a miRNA sequence that downregulates production of TNF-α. The AAV vector is comprised of AAV2 inverted terminal repeats (ITRs), a composite CASI promoter, a human growth hormone (HGH) signal peptide followed by a miR155 microRNA cassette containing three different siRNAs targeting murine TNF-60, a woodchuck hepatitis virus post-transcriptional regulatory element (WPRE), and an SV40 polyA signal.

```
SEQ ID No. 1 (whole RP):
cagcagctgc gcgctcgctc gctcactgag gccgcccggg caaagcccgg gcgtcgggcg    60
acctttggtc gcccggcctc agtgagcgag cgagcgcgca gagagggagt ggccaactcc   120
atcactaggg gttccttgta gttaatgatt aacccgccat gctacttatc tacgtagcca   180
tgctctagga cattgattat tgactagtgg agttccgcgt tacataactt acggtaaatg   240
gcccgcctgg ctgaccgccc aacgaccccc gcccattgac gtcaataatg acgtatgttc   300
ccatagtaac gccaataggg actttccatt gacgtcaatg ggtggagtat ttacggtaaa   360
ctgcccactt ggcagtacat caagtgtatc atatgccaag tacgccccct attgacgtca   420
atgacggtaa atggcccgcc tggcattatg cccagtacat gaccttatgg gactttccta   480
cttggcagta catctacgta ttagtcatcg ctattaccat ggtcgaggtg agccccacgt   540
tctgcttcac tctccccatc tccccccct ccccacccc aattttgtat ttatttattt   600
tttaattatt ttgtgcagcg atggggggcgg gggggggggg gggcgcgcgc caggcggggc   660
ggggcggggc gagggcgggg gcggggcgag gcggagaggt gcggcggcag ccaatcagag   720
cggcgcgctc cgaaagtttc cttttatggc gaggcggcgg cggcggcggc cctataaaaa   780
gcgaagcgcg cggcgggcgg gagtcgctgc gcgctgcctt cgccccgtgc cccgctccgc   840
cgccgcctcg cgccgcccgc cccggctctg actgaccgcg ttactaaaac aggtaagtcc   900
ggcctccgcg ccgggttttg gcgcctcccg cgggcgcccc cctcctcacg gcgagcgctg   960
ccacgtcaga cgaagggcgc agcgagcgtc ctgatccttc cgcccggacg ctcaggacag  1020
cggcccgctg ctcataagac tcggccttag aaccccagta tcagcagaag gacattttag  1080
gacgggactt gggtgactct agggcactgg ttttctttcc agagagcgga acaggcgagg  1140
aaaagtagtc ccttctcggc gattctgcgg agggatctcc gtgggcggt gaacgccgat  1200 gatgcctcta ctaaccatgt tcatgttttc ttttttttc tacaggtcct gggtgacgaa  1260
caggcctagc atcgataccg tcgtatgtgc tggaggcttg ctgaaggctg tatgctggct  1320
```

-continued

```
cctccacttg gtggtttggt tttggcctct gactgaccaa accacagtgg aggagccagg   1380
acacaaggcc tgttactagc actcacatgg aacaaatggc ctctagcctg gaggcttgct   1440
gaaggctgta tgctgtttct cctggtatga gatagcgttt tggcctctga ctgacgctat   1500
ctcaccagga gaaacaggac acaaggcctg ttactagcac tcacatggaa caaatggcct   1560
ctagcctgga ggcttgctga aggctgtatg ctgccgcaaa gtctaagtac ttgggttttg   1620
gcctctgact gacccaagta cagactttgc ggcaggacac aaggcctgtt actagcactc   1680
acatggaaca aatggcctct ctagaataat caacctctgg attacaaaat ttgtgaaaga   1740
ttgactggta ttcttaacta tgttgctcct tttacgctat gtggatacgc tgctttaatg   1800
cctttgtatc atgctattgc ttcccgtatg gctttcattt tctcctcctt gtataaatcc   1860
tggttgctgt ctctttatga ggagttgtgg cccgttgtca ggcaacgtgg cgtggtgtgc   1920
actgtgtttg ctgacgcaac ccccactggt tggggcattg ccaccacctg tcagctcctt   1980
tccgggactt tcgctttccc cctccctatt gccacggcgg aactcatcgc cgcctgcctt   2040
gcccgctgct ggacaggggc tcggctgttg ggcactgaca attccgtggt gttgtcgggg   2100
aaatcatcgt cctttccttg ctgctcgcc tgtgttgcca cctggattct gcgcgggacg   2160
tccttctgct acgtcccttc ggccctcaat ccagcgacc ttccttcccg cggcctgctg   2220
ccggctctgc ggcctcttcc gcgtcttcgc cttcgccctc agacgagtcg gatctccctt   2280
tgggccgcct cccgcctaa gcttatcgat accgtcgaga tctaacttgt ttattgcagc   2340
ttataatggt tacaaataaa gcaatagcat cacaaatttc acaaataaag catttttttc   2400
actgcattct agttgtggtt tgtccaaact catcaatgta tcttatcatg tctggatctc   2460
gacctcgact agagcatggc tacgtagata agtagcatgg cgggttaatc attaactaca   2520
aggaacccct agtgatggag ttggccactc cctctctgcg cgctcgctcg ctcactgagg   2580
ccgggcgacc aaaggtcgcc cgacgcccgg gctttgcccg gcggcctca gtgagcgagc   2640 gagcgcgcag ctggcgtaat agcgaagagg cccgcaccga tcgcccttcc caacagttgc   2700
gcagcctgaa tggcgaatgg cgattccgtt gcaatggctg cggtaatat tgttctggat   2760 attaccagca aggccgatag tttgagttct tctactcagg caagtgatgt tattactaat   2820
caaagaagta ttgcgacaac ggttaatttg cgtgatggac agactctttt actcggtggc   2880
ctcactgatt ataaaaacac ttctcaggat tctggcgtac cgttcctgtc taaaatccct   2940
ttaatcggcc tcctgtttag ctcccgctct gattctaacg aggaaagcac gttatacgtg   3000
ctcgtcaaag caaccatagt acgcgccctg tagcggcgca ttaagcgcgg cgggtgtggt   3060
ggttacgcgc agcgtgaccg ctacacttgc cagcgcccta gcgcccgctc ctttcgcttt   3120
cttcccttcc tttctcgcca cgttcgccgg ctttccccgt caagctctaa atcggggct   3180 cccctttaggg ttccgattta gtgctttacg gcacctcgac cccaaaaaac ttgattaggg   3240
tgatggttca cgtagtgggc catcgccctg atagacggtt tttcgccctt tgacgttgga   3300
gtccacgttc tttaatagtg gactcttgtt ccaaactgga acaacactca accctatctc   3360
ggtctattct tttgatttat aagggatttt gccgatttcg gcctattggt taaaaaatga   3420
gctgatttaa caaaaattta acgcgaattt taacaaaata ttaacgttta caatttaaat   3480
atttgcttat acaatcttcc tgttttttggg gcttttctga ttatcaaccg gggtacatat   3540
gattgacatg ctagttttac gattaccgtt catcgattct cttgtttgct ccagactctc   3600
aggcaatgac ctgatagcct ttgtagagac ctctcaaaaa tagctaccct ctccggcatg   3660
```

-continued

```
aatttatcag ctagaacggt tgaatatcat attgatggtg atttgactgt ctccggcctt    3720
tctcacccgt ttgaatcttt acctacacat tactcaggca ttgcatttaa aatatatgag    3780
ggttctaaaa atttttatcc ttgcgttgaa ataaaggctt ctcccgcaaa agtattacag    3840
ggtcataatg ttttttggtac aaccgattta gctttatgct ctgaggcttt attgcttaat    3900
tttgctaatt ctttgccttg cctgtatgat ttattggatg ttggaattcc tgatgcggta    3960
ttttctcctt acgcatctgt gcggtatttc acaccgcata tggtgcactc tcagtacaat    4020
ctgctctgat gccgcatagt taagccagcc ccgacacccg ccaacacccg ctgacgcgcc    4080
ctgacgggct tgtctgctcc cggcatccgc ttacagacaa gctgtgaccg tctccgggag    4140
ctgcatgtgt cagaggtttt caccgtcatc accgaaacgc gcgagacgaa agggcctcgt    4200
gatacgccta ttttttatagg ttaatgtcat gataataatg gtttcttaga cgtcaggtgg    4260
cacttttcgg ggaaatgtgc gcggaacccc tatttgttta ttttttctaaa tacattcaaa    4320 tatgtatccg ctcatgagac aataaccctg ataaatgctt caataatatt gaaaaaggaa    4380
gagtatgagt attcaacatt tccgtgtcgc ccttattccc ttttttgcgg cattttgcct    4440
tcctgttttt gctcacccag aaacgctggt gaaagtaaaa gatgctgaag atcagttggg    4500
tgcacgagtg ggttacatcg aactggatct caacagcggt aagatccttg agagttttcg    4560
ccccgaagaa cgttttccaa tgatgagcac ttttaaagtt ctgctatgtg gcgcggtatt    4620
atcccgtatt gacgccgggc aagagcaact cggtcgccgc atacactatt ctcagaatga    4680
cttggttgag tactcaccag tcacagaaaa gcatcttacg gatggcatga cagtaagaga    4740
attatgcagt gctgccataa ccatgagtga taacactgcg gccaacttac ttctgacaac    4800
gatcggagga ccgaaggagc taaccgcttt tttgcacaac atgggggatc atgtaactcg    4860
ccttgatcgt tgggaaccgg agctgaatga agccatacca aacgacgagc gtgacaccac    4920
gatgcctgta gcaatggcaa caacgttgcg caaactatta actggcgaac tacttactct    4980
agcttcccgg caacaattaa tagactggat ggaggcggat aaagttgcag gaccacttct    5040
gcgctcggcc cttccggctg gctggtttat tgctgataaa tctggagccg gtgagcgtgg    5100
gtctcgcggt atcattgcag cactggggcc agatggtaag ccctcccgta tcgtagttat    5160
ctacacgacg gggagtcagg caactatgga tgaacgaaat agacagatcg ctgagatagg    5220
tgcctcactg attaagcatt ggtaactgtc agaccaagtt tactcatata ctttttagat    5280
tgatttaaaa cttcattttt aatttaaaag gatctaggtg aagatccttt ttgataatct    5340
catgaccaaa atcccttaac gtgagttttc gttccactga gcgtcagacc ccgtagaaaa    5400
gatcaaagga tcttcttgag atcctttttt tctgcgcgta atctgctgct tgcaaacaaa    5460
aaaaccaccg ctaccagcgg tggtttgttt gccggatcaa gagctaccaa ctctttttcc    5520
gaaggtaact ggcttcagca gagcgcagat accaaatact gtccttctag tgtagccgta    5580
gttaggccac cacttcaaga actctgtagc accgcctaca tacctcgctc tgctaatcct    5640
gttaccagtg gctgctgcca gtggcgataa gtcgtgtctt accgggttgg actcaagacg    5700
atagttaccg gataaggcgc agcggtcggg ctgaacgggg ggttcgtgca cacagcccag    5760
cttggagcga acgacctaca ccgaactgag atacctacag cgtgagctat gagaaagcgc    5820
cacgcttccc gaagggagaa aggcggacag gtatccggta agcggcaggg tcggaacagg    5880
agagcgcacg agggagcttc caggggggaaa cgcctggtat ctttatagtc ctgtcgggtt    5940
tcgccacctc tgacttgagc gtcgattttt gtgatgctcg tcaggggggc ggagcctatg    6000
gaaaaacgcc agcaacgcgg ccttttacg gttcctggcc ttttgctggc cttttgctca    6060
catgttcttt cctgcgttat cccctgattc tgtggataac cgtattaccg cctttgagtg    6120
```

```
                                       -continued
agctgatacc gctcgccgca gccgaacgac cgagcgcagc gagtcagtga gcgaggaagc    6180
ggaagagcgc ccaatacgca aaccgcctct ccccgcgcgt tggccgattc attaatg      6237

SEQ ID No. 2(miRNA cassette):
ctggaggctt gctgaaggct gtatgctggc tcctccactt ggtggtttgg ttttggcctc    60
tgactgacca aaccacagtg gaggagccag gacacaaggc ctgttactag cactcacatg   120
gaacaaatgg cctctagcct ggaggcttgc tgaaggctgt atgctgtttc tcctggtatg   180
agatagcgtt ttggcctctg actgacgcta tctcaccagg agaaacagga cacaaggcct   240
gttactagca ctcacatgga acaaatggcc tctagcctgg aggcttgctg aaggctgtat   300
gctgccgcaa agtctaagta cttgggtttt ggcctctgac tgacccaagt acagactttg   360
cggcaggaca caaggcctgt tactagcact cacatggaac aaatggcctc tctagaa     417

SEQ ID No. 3 (miRNA 1):
ctggaggctt gctgaaggct gtatgctggc tcctccactt ggtggtttgg ttttggcctc    60
tgactgacca aaccacagtg gaggagccag gacacaaggc ctgttactag cactcacatg   120
gaacaaatgg cctctagcc                                                139

SEQ ID No. 4 (miRNA 2):
tggaggcttg ctgaaggctg tatgctgttt ctcctggtat gagatagcgt tttggcctct    60
gactgacgct atctcaccag gagaaacagg acacaaggcc tgttactagc actcacatgg   120
aacaaatggc ctctagc                                                  137

SEQ ID No. 5 (miRNA 3):
ctggaggctt gctgaaggct gtatgctgcc gcaaagtcta agtacttggg ttttggcctc    60
tgactgaccc aagtacagac tttgcggcag gacacaaggc ctgttactag cactcacatg   120
gaacaaatgg cctctctaga a                                             141
```

SEQ ID No. 6 (miRNA 1 anti-sense)
gctcctccac ttggtggttt g        21

SEQ ID No. 7 (miRNA 1 sense)
caaaccacag tggaggagc           19

SEQ ID No. 8 (miRNA 2 anti-sense)
tttctcctgg tatgagatag c        21

SEQ ID No. 9 (miRNA 2 sense)
gctatctcac caggagaaa           19

SEQ ID No. 10 (miRNA 3 anti-sense)
ccgcaaagtc taagtacttg g        21

SEQ ID No. 11 (miRNA 3 sense)
ccaagtacag actttgcgg           19

Example 1—Expression Cassette

Figure 9:
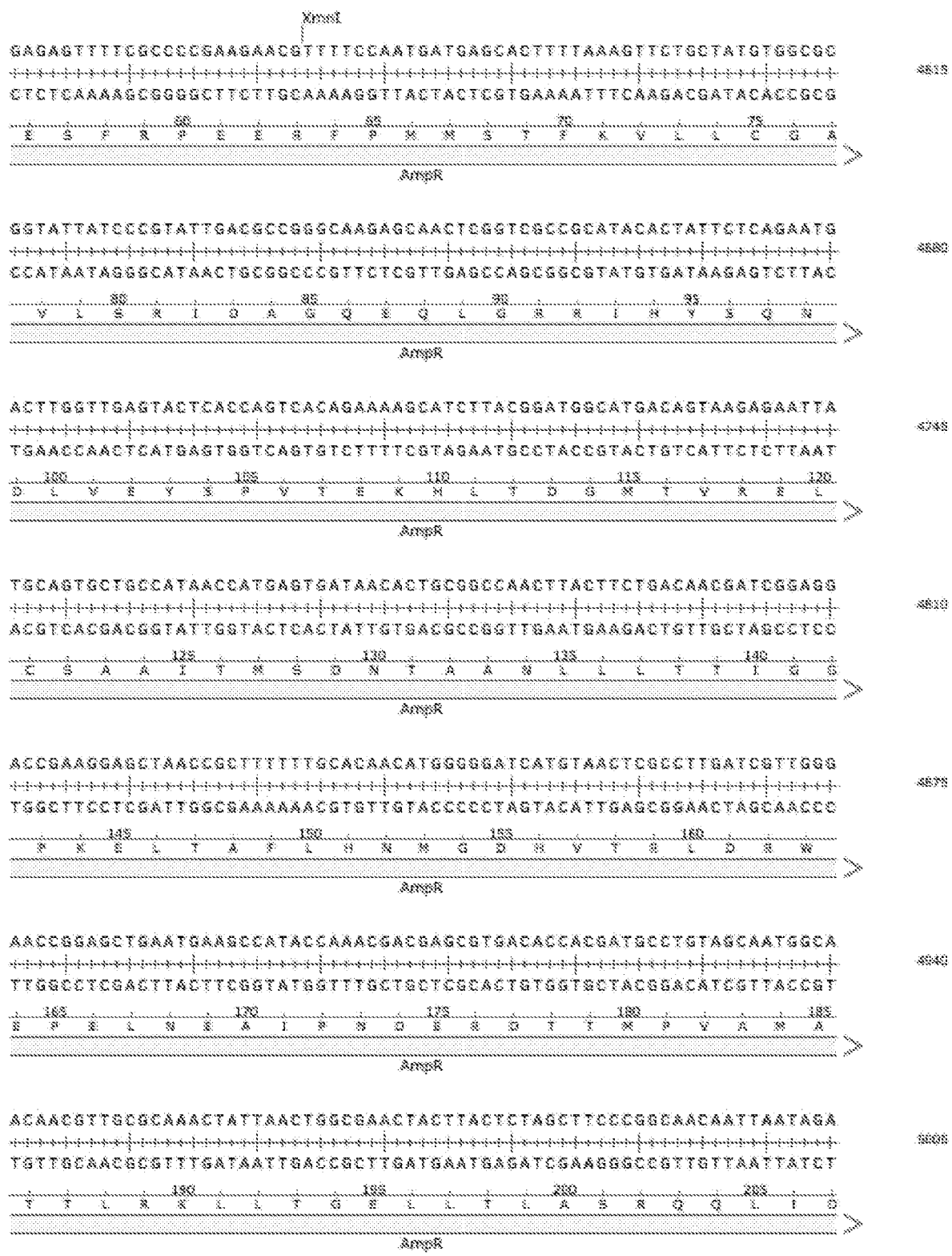
FIG. 9 is a schematic that represents a ninth portion of an RP, according to embodiments of the present disclosure, which is contiguous with the eighth portion of FIG. 8.

Expression cassettes for expressing a monoclonal antibody (mAb) and/or a protein and/or miRNA were synthesized. Each cassette contained a signal peptide, the variable heavy domain, the human IgG1 constant domain, the protein or the miRNA sequence followed by (when it is an Ab), a self-cleaving 2A peptide sequence, a signal peptide, the variable light domain and the human lambda constant domain. The synthesized mAb and/or protein and/or miRNA expression cassettes were cloned into the pAVA-00200 plasmid backbone containing the CASI promoter1, multiple cloning site (MCS), Woodchuck Hepatitis Virus post-transcriptional regulatory element (WPRE), Simian virus 40 (SV40) polyadenylation (polyA) sequence all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each mAb and/or protein and/or miRNA expression cassette was amplified by PCR using Taq polymerase and the PCR products were gel purified and the bands on interest were also excised and purified using a gel extraction kit. These PCR products contained the mAb and/or protein and/or miRNA expression cassettes in addition to 15 base pair 5' and 3' overhangs that align with the ends of the linearized pAVA-00200 backbone. Using in-fusion cloning2, the amplified mAb or protein or miRNA expression cassettes are integrated with the pAVA-00200 backbone via homologous recombination. The resulting RP contained the following 5' ITR, CASI promoter, monoclonal antibody or protein or miRNA expression cassette, WPRE, SV40 polyA and ITR 3', per SEQ ID No. 1 and as shown in the contiguous portions of FIG. 1 through FIG. 12.

The invention claimed is:

1. A composition comprising a nucleotide sequence of SEQ ID No. 1.

2. The composition of claim 1, wherein the composition is a recombinant plasmid (RP).

3. The composition of claim 2, wherein the RP is for use in a vector.

4. The composition of claim 3, wherein the vector can be an enveloped virus, an unenveloped virus, a replication effective virus, a replication ineffective virus and combinations thereof.

5. The composition of claim 4, wherein the virus is of the Paroviridae family.

6. The composition of claim 4, wherein the virus is of the Dependoparvovirus family.

7. The composition of claim 3, the vector is an adeno-associated virus (AAV).

8. The composition of claim 3, wherein the vector is a recombinant AAV.

9. The composition of claim 3, wherein the vector is a recombinant AAV6.2FF.

10. A composition comprising a nucleotide sequence of SEQ ID No. 2.

11. A composition comprising a nucleotide sequence of SEQ ID No. 3.

12. A composition comprising a nucleotide sequence of SEQ ID No. 4.

13. A method of making an composition/target cell complex, the method comprising a step of administering a RP comprising SEQ ID No. 1 to a target cell for forming the composition/target cell complex, wherein the composition/target cell complex causes the target cell to increase production of a one or more sequences of micro ribonucleic acid (miRNA) that decreases production of a target biomolecule.

14. The method of claim 13, wherein the target biomolecule is a target cytokine.

15. The method of claim 14, wherein the target cytokine is a tumor necrosis factor alpha (TNF-alpha).

16. The method of claim 13, wherein the target cell is one or more of an adrenal gland cell; a B cell; a bile duct cell; a chondrocyte; a cochlear cell; a corneal cell; a dendritic cell, an endocardium cell; an endometrial cell; an endothelial cell; an epithelial cell; an eosinophil; a fibroblast; a hair follicle cell; a hepatocyte; a lymph node cell; a macrophage; a mucosal cell; a myocyte; a neuron; a glomeruli cell; an optic nerve cell; an osteoblast; an ovarian tissue cell; a pancreatic islet beta cell; a pericardium cell; a platelet; a red blood cell (RBC); a retinal cell; a scleral cell; a Schwann cell; a stem cell, a T cell; a testicular tissue cell; a thyroid gland cell; an uveal cell; and combinations thereof.

* * * * *